United States Patent [19]
Lukić

[11] Patent Number: 5,892,036
[45] Date of Patent: Apr. 6, 1999

[54] PROCESS FOR THE PREPARATION OF 2-BROMO- AND 2-NITROXY DERIVATIVES OF 3-BROMO- AND 3,3-DIBROMO-4-OXO-AZETIDINES

[75] Inventor: Irena Lukić, Zagreb, Croatia

[73] Assignee: PLIVA farmaceutska, Zagreb, Croatia

[21] Appl. No.: 926,449

[22] Filed: Sep. 10, 1997

Related U.S. Application Data

[60] Continuation of Ser. No. 500,414, Jul. 10, 1995, abandoned, which is a division of Ser. No. 272,206, Jul. 8, 1994, Pat. No. 5,670,638.

[30] Foreign Application Priority Data

Jul. 9, 1993 [HR] Croatia ............................ P 93 1047 A

[51] Int. Cl.$^6$ ........................ C07D 205/08; A61K 31/395
[52] U.S. Cl. ............................................ 540/354; 540/361
[58] Field of Search ...................... 540/354, 361

[56] References Cited

U.S. PATENT DOCUMENTS 5,075,439  12/1991  Busch et al. ............................ 540/359

OTHER PUBLICATIONS

Brain, J. Chem. Soc. Perkins I, 447 (1976).
Maruyama, J Org Chem 51, 399 (1986).
Kovacevic, Croat. Chem Acta 65, 817 (1992).

*Primary Examiner*—Mark Berch
*Attorney, Agent, or Firm*—Pollock, Vande Sande & Amernick

[57] ABSTRACT

The invention relates to novel 2-bromo- and 2-nitroxy derivatives of 3-,bromo- and 3-dibromo-4-oxo-azetidines, to processes for the preparation thereof and to the use thereof.

According to the invention 2-bromo- and 2-nitroxy derivatives of 3-bromo- and 3-dibromo-4-oxo-azetidines are prepared by reacting derivatives of protected penicillanic lanic acid 1,1-dioxides with DBN reactant (1,5-diazabicyclo/3.4.0/non-5-ene) and then the obtained DBN salt of sulfinic acid or isolated sulfinic acid is treated with thionyl chloride and, after eliminating thionyl chloride by evaporation, the obtained residue is passed through a silica gel column with methylene chloride or some other solvent as eluant or the obtained residue is dissolved in tetrahydrofuran or some other suitable solvent and treated with tetrabutyl ammonium bromide and after the treatment a derivative of 2-bromo, 3-bromo or 2-bromo-3,3-dibromo-4oxo-azetidine is isolated, which derivative may be subjected to a reaction with silver nitrate in 2-propanol and, after the treatment of the reaction mixture, derivatives of 2-nitroxy-, 3-bromo- or 2-nitroxy-3,3-dibromo-4-oxo-azetidine are isolated.

The obtained substances are useful intermediates in the syntheses of beta lactam analogons or as components in formulations having antibacterial, inhibitory, anti-tumour or antagonistic action.

19 Claims, No Drawings

PROCESS FOR THE PREPARATION OF 2-BROMO- AND 2-NITROXY DERIVATIVES OF 3-BROMO- AND 3,3-DIBROMO-4-OXO-AZETIDINES

This application is a continuation of U.S. patent application Ser. No. 08/500,414, filed Jul. 10, 1995, abandoned which is a divisional of U.S. patent application Ser. No. 08/272,206, filed Jul. 8, 1994, now U.S. Pat. No. 5,670,638.

TECHNICAL FIELD

IPC: C07D 205/08

A 61K 31/395

The invention relates to 2-bromo- and 2-nitroxy derivatives of 3-bromo- and 3, 3-dibromo-4-oxo-azetidines, to processes for the preparation thereof and to the use thereof.

There are known certain 2-chloro derivatives of 3-phthalimido-alpha-(1-methyl-ethylidene)-4-oxo-1-azetidine acetic acid, which are prepared by reacting methyl-6-phthalimido penicillanate with chlorine or sulfuryl chloride (Kukolja S., J. Am. Chem. Soc. 93, (1971), 6267).

Haloazetidinones are also prepared by reacting penicillin with halogenating agents such as molecular chlorine or N-halosuccinimide (U.S. Pat. No. 4,159,984). Further, there is disclosed the rearrangement of oxoazetidine sulfinic acids obtained from penicillin sulfoxide, with halogenating agents into haloazetidinones (Spitzer W. A., Kukolja S., Goodson T., Lammert J. P., Steven R., Lilly Eli Co., EP 60 120, equivalent U.S. Pat. No. 4,368,156; Spitzer W. A., Goodson T., Lammert S. R. and Kukolja S. J., Org. Chem. 46, (1981) 3569). Narisada et al. disclosed the synthesis of chloroazetidinone from methylthioazetidinones obtained from penicillin (U.S. Pat. No. 4,138,486).

S. Kukolja and S. R. Lammert further disclosed the preparation of the abovementioned 2-chloro derivatives starting from trichloroethyl ester of 6-phenyl-acetamido-penicillanate (Croat. Chem. Acta 44, (1972) 299–301). The Eli Lilly Company claimed the preparation of haloazetidinones starting from 3-exomethylene cephalosporin sulfone with the acylamide group in the 7-position and reacting the same with activated zinc or magnesium and ammonium chloride to obtain sulfinic acids, which acids with halogenating agents give sulfinyl chlorides, which are then subjected to hydrolysis (EP 132395).

3-bromo- and 3,3-dibromo-2-chloroazetidinones are also prepared by the reaction of pivaloyloxymethyl 6-bromo- or 6,6-dibromopenicillanate with chlorine or tertiary butyl hypochlorite (C. Somoza and O. A. Oreste, Tetrahedron 44, (1988) 7007–12.).

According to our knowledge 2-bromo- and 2-nitroxy derivatives of 3-bromo- and 3,3-dibromo-4-oxo-azetidines are not known.

The object of the present invention are 2-bromo- and 2-nitroxy derivatives of 3-bromo- and 3,3-dibromo-4-oxo-azetidines of the general formula I

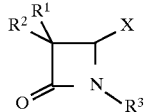

wherein $R^1$ is hydrogen or bromine, $R^2$ is hydrogen or bromine, $R^3$ is hydrogen;

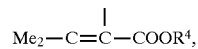

wherein $R^4$ is hydrogen, methyl, benzyl or some other carboxy-protective group, and X is bromine or nitroxy group (—ONO$_2$).

A further object of the present invention is a process for preparing 2-bromo- and 2-nitroxy derivatives of 3-bromo- and 3,3-dibromo-4-oxo-azetidines of the general formula I, wherein the radicals have the above meaning, starting from derivatives of penicillanic acid 1,1-dioxides of the general formula II

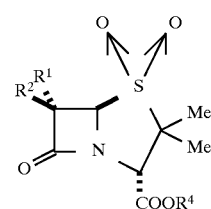

wherein radicals $R^1$ and $R^2$ have the above meaning and $R^4$ is methyl or benzyl or some other protective group, by reacting with DBN (1,5-diazabicyclo/3.4.0/non-5-ene) and then the obtained DBN salt of sulfinic acid or isolated suifinic acid is treated with tionyl chloride and, after eliminating thionyl chloride by evaporation, the obtained residue is passed through a silica gel column with methylene chloride as eluant or the obtained residue is dissolved in tetrahydrofuran and treated with tetrabutyl ammonium bromide and after the treatment a derivative of the general formula I wherein $R^1$ is hydrogen or bromine, $R^2$ is hydrogen or bromine, $R^3$ is hydrogen;

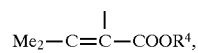

wherein $R^4$ is hydrogen, methyl, benzyl or some other carboxy-protective group, and X is bromine, is isolated.

The obtained 2-bromo derivatives of the general formula I wherein $R^4$ is e.g. benzyl, are converted, by eliminating the benzyl group with aluminum trichloride, into a product I wherein $R^4$ is hydrogen, or are subjected to the reaction with silver nitrate in isopropanol to obtain the derivative of the general formula I wherein X is nitroxy group and $R^4$ is benzyl.

The derivatives of 6,6-dibromopenicillanic acid are prepared from 6-amino-penicillanic acid according to known processes (R. A. Volkmann, R. D. Carrol, R. B. Drolet, M. L. Elliott and B. S. Moore, J. Org. Chem. 47 (1982) 3344–5; Wayne E. Barth, U.S. Pat. No. 4,234,579).

A further object of the present invention is the use of these compounds as useful intermediates in preparing various beta lactam analogons such as 1-oxapenems(Masyuki Murakami, Tsutomu Auki, Munenuri Matasura and Wataru Nagata, J. Antibiot. 43 (1990) 1441–49; H. R. Pfaendler, T. Neumann and R. Bartsch, Synthesis (1992) 1179) or penems (V. M. Girijavallabhan, A. K. Ganguly, S. W. McCombie, P. Pinto, R. Rizvi, Tetrahedron Lett. 22, (1981) 3485–88; C. M. D. Beels, M. S. Abu Rabie, J. Chem. Soc. Chem. Commun. 1979, 665) or 1-oxacephalosporins (U.S. Pat. No. 4,013,653, U.S. Pat. No. 4,234,724, U.S. Pat. No. 4,159,984) or the present invention offers great possibilities for transformations into other monobactams or cyclic compounds. Additionally, the corresponding 2-nitroxy derivatives of azetidinones are also potential $Ca^{++}$ antagonists such as are also nitroglycerin, nicorandil or nipradiol.

A further object of the present invention is the use of these compounds as raw materials in formulations having antibacterial, inhibitory, antitumour and antagonistic action.

Some of the compounds of the general formula I in concentrations of about $10^{-5}M$ inhibit the growth of tumour cells of human cervix uteri (HeLa) by as much as 70% whereas they do not exhibit any action on normal fibroblasts (WI38).

The presently disclosed knowledge about antitumour action of these as well as some other analogues (e.g. 3,3-dibromo-2-chloro-alpha-(1-methylethylidene)-4-oxo-azetidine-1-acetic acid) represents novel knowledge about biological activity of beta lactams.

The invention is illustrated by the following Examples which are in no way limitative as to the scope thereof.

EXAMPLE 1

2,3,3-tribromo-alpha-(1-methylethylidene)-4-oxo-1-azetidine acetic acid benzyl ester 6,6-dibromopenicillanic acid sulfone benzyl ester (4.8 g; 0.01 mole) was dissolved in methylene chloride (50 ml) and 1.5-diaza-bicyclo[4.3.0]non-5-ene (2.08 g; 2 ml; 0.0167 mole) was added. The reaction mixture was stirred for half an hour at room temperature, then cooled to 0° to 5° C., thionyl chloride (24.5 g; 15 ml; 0.205 mole) was added drop by drop, it was stirred for half an hour at this temperature and for another hour at room temperature. The reaction mixture was evaporated to a dry residue, benzene (15 ml) was added and it was again evaporated to a dry residue. The obtained product was passed through a silica gel column with methylene chloride followed by the isolation of the substance (1.08 g; 21.8%).

m.p. 68°–70° C. Rf 0.72 (methylene chloride); IR (KBr): 1795(vs), 1730(s), 1635(m), 1395(m), 1375(m), 1270(m), 1225(vs), 1125–1070(m), 815(m), 700(m) $cm^{-1}$. $^1H$ NMR ($CDCl_3$)δ: 2.00 (3H, s, Me), 2.34 (3H, s, Me), 5.16 and 5.25 (each 1H d, J=12 Hz, $CH_2Ph$), 6.30 (1H, s, $C_2$–H), 7.36 (5H, s, Ar) ppm. $^{13}C$ ($CDCl_3$) APT: 22.352 and 23.875 (2 Me), 55.675 ($C_3$—$Br_2$), 67.441 ($CH_2Ph$), 74.084 ($C_2$—H), 117.031 (N—C=), 128.784 (Ph), 135.112 (C—Ph), 158.071 (COO), 159.948 (=$C(Me)_2$), 162.283 (C=O). Analysis for $Cl_{15}H_{14}Br_3NO_3$: calc.: C 36.32; H 2.84; N 2.82% found: C 36.61; H 2.75; N 2.76% Mol. mass: 496.018; m/e 477 (—$H_2O$), 416 (—Br), 404(—$CH_2Ph$).

EXAMPLE 2

2,3,3-tribromo-alpha-(1-methylethylidene)-4-oxo-1-azetidine acetic acid benzyl ester 6,6-dibromopenicillanic acid sulfone benzyl ester (3.84 g; 0.008 mole) was dissolved in methylene chloride (40 ml) and 1.5-diaza-bicyclo[4.3.0]non-5-ene (1.66 g; 1.6 ml; 0.013 mole) was added. The reaction mixture was stirred for half an hour at room temperature. The obtained solution was treated with 0.1N hydrochloric acid and NaCl, the layers were separated, the aqueous one was extracted two more times with methylene chloride, dried and evaporated to dryness. To the evaporated residue a solution of thionyl chloride (12 ml) in methylene chloride (40 ml) was added, it was stirred for half an hour at room temperature, evaporated to a dry residue, benzene (2×30 ml) was added and it was again evaporated to dryness. The obtained residue was dissolved in tetrahydrofuran (120 ml), tetrabutylammonium bromide (2.576 g; 0.008 mole) was added and it was stirred at room temperature up to the disappearance of the starting substance (TLC). The solution was then evaporated to dryness and was passed through a silica gel column with methylene chloride as eluant. Combined fractions with Rf 0.72 (methylene chloride) were evaporated and treated with n-hexane to give a product with m.p. 71°–72° C. (1.48 g; 37.75%). The remaining spectroscopic data were identical as in Example 1.

EXAMPLE 3

2,3,3-tribromo-alpha-(1-methylethylidene)-4oxo-1-azetidine acetic acid methyl ester 6,6-dibromopenicillanic acid sulfone methyl ester (0.810 g; 0.002 mole) was dissolved in methylene chloride (10 ml) and 1.5-diaza-bicyclo [4.3.0]non-5-ene (0.4 g; 0.4 ml; 0.0033 mole) was added. The reaction mixture was stirred for half an hour at room temperature, then cooled to 0° to 5° C., thionyl chloride (4.9 g; 3 ml; 0.040 mole) was added drop by drop, it was stirred for half an hour at this temperature and for another hour at room temperature. The reaction mixture was evaporated to a dry residue, benzene (15 ml) was added and it was again evaporated to a dry residue. The obtained product was passed through a silica gel column with methylene chloride followed by isolation of the substance (0.198 g; 23.6%).

m.p. 68°–70° C. Rf 0.56 (methylene chloride); IR (film): 1805(vs), 1735(vs), 1640(m), 1440(m), 1385(vs), 1370(vs), 1270(s) 1230(vs), 1125–1070(bs), 815 (s) $cm^{-1}$. $^1H$ NMR ($CDCl_3$)(300 MHz)δ: 2.01 (3H, s, Me), 2.33 (3H, s, Me), 3.01 (s, 3H, $OCH_3$) 6.42 (s, 1H, $C_2$—H) ppm. $^{13}C$ ($CDCl_3$) APT: 22.286 and 23.815 (2 Me), 52.270 ($OCH_3$), 55.761 ($C_3$—$Br_2$), 74.020 ($C_2$—H), 116.985 (N—C=), 159.275 (COO), 159.561 (=$C(Me)_2$), 162.865 (C=O). Brutto formula $C_9H_{10}Br_3NO_3$ Mol. mass: 419.926; $M^+420$, m/e 389 (—$OCH_3$), 340 (—Br).

EXAMPLE 4

3,3-dibromo-2-chloro-alpha-(1-methylethylidene)-4-oxo-1-azetidine acetic acid benzyl ester 6,6-dibromopenicillanic acid sulfoxide benzyl ester (6.96 g; 0.015 mole) was dissolved in toluene (750 ml), N-chlorosuccinimide (4.02 g; 0.030 mole) was added and it was heated in a nitrogen current at the boiling temperature for 1.5 hours. After the reaction was completed, hydrochloric acid (1N, 450 ml) was added and the solution was refluxed under refluxing condenser for one hour. The layers were separated, the toluene layer was washed with water, dried ($CaCl_2$) and evaporated to dryness (5.76 g; 85.2% of the crude product). The obtained product was dissolved in methylene chloride (50 ml), triethylamine (1.5 g; 2.1 ml) was added to the solution and it was stirred at room temperature for 10 minutes. Water was added to the reaction mixture, the pH was adjusted to 5 to 6, the organic layer was washed with water, dried ($Na_2SO_4$) and evaporated to dryness. The obtained product was passed through a silica gel column with methylene chloride as eluant, followed by isolating the product (1.98 g; 30%) by means of n-hexane.

m.p. 64°–66° C. Rf 0.70 (methylene chloride); IR (KBr) v: 1795(vs), 1730(s), 1635(m), 1395(m), 1375(m), 1270(vs), 1220(s), 1125–1070(b,m), 820(m), 700(m) $cm^{-1}$. $^1HNMR$ ($CDCl_3$)(300 MHz) δ: 2.00 and 2.35 (2s, 6H, 2Me), 5.16 and 5.25 (each 1H, d, J=12 Hz, $CH_2Ph$), 6.06 (s, 1H, $C_2$—H), 7.37 (s, 5H, Ar) ppm. $^{13}C$ ($CDCl_3$) APT: 22.281 and 23.808 (2 Me), 56.555 ($C_3$—$Br_2$), 67.433 ($CH_2Ph$) 81.305 ($C_2$—H), 116.748 (N—C=), 128.941 (Ph), 135.130 (C—Ph), 158.509 (COO), 160.273 (=$C(Me)_2$). Mol. mass: 451.558; m/e 433 (—H2O); 416 (—Cl); 360 (—$CH_2Ph$).

EXAMPLE 5

3,3-dibromo-alpha-(1-methylethylidene)-2-nitroxy-4-oxo-1-azetidine acetic acid benzyl ester 2,3,3-tribromo-alpha-(1- methylethylidene)-4-oxo-1-azetidine acetic acid benzyl ester (0.744 g; 0.0015 ml) was dissolved in 2-propanol (20 ml), silver nitrate (1.01 g; 0.0060 mole) was added thereto and it was heated in a nitrogen current at the boiling temperature for 1 hour. Then the reaction mixture was filtered and the filtrate was evaporated to dryness. Methylene chloride was added to the evaporated residue, the precipitate was sucked off and the filtrate was evaporated to dryness (0.466 g; 65%). The obtained product was passed through a silica gel column with methylene chloride, followed by the isolation of a substance which crystallized upon standing (0.418 g; 58.13%).

m.p. 69°–71° C. Rf=0.75 (methylene chloride); IR (KBr): 1805(vs), 1730(vs), 1660(vs), 1390(m), 1375(m), 1285(vs), 1225(vs), 1140(s), 1080(m), 830(s), 760 (m), 700(m) cm$^{-1}$. $^1$H NMR (CDCl$_3$)(300 MHz) δ: 1.99 (3H, s, Me), 2,32 (3H, s, Me), 5.16 and 5.27 (each 1H d, J=12 Hz, CH$_2$Ph), 6.42 (1H, s, C$_2$—H), 7.37 (5H, s, Ar) ppm. $^{13}$C (CDCl$_3$) APT: 21.973 and 23.700 (2 Me), 52.935 (C$_3$—Br$_2$), 67.344 (CH$_2$—Ph), 90.895 (C$_2$—H), 116.654 (N—C=), 128.613 (Ph), 134.660 (C—Ph), 158.290 (COO), 159.634 (=C(Me)$_2$), 161.669 (C=O). Mol. mass: 478.11; m/e 432 (—NO$_2$); 398 (—Br); 352 (—NO$_2$).

EXAMPLE 6

3,3-dibromo-alpha-1-(1-methylethylidene)-2-nitroxy-4-oxo-1-azetidine acetic acid benzyl ester 3,3-dibromo-alpha-(1-methylethylidene)-2-nitroxy-4-oxo-1-azetidine acetic acid benzyl ester could be obtained in an analogous way as in Example 5 with the difference that the starting substance was 3,3-dibromo-alpha-(1-methylethylidene)-2-chloro-4-oxo-1-azetidine acetic acid benzyl ester.

EXAMPLE 7

2,3,3-tribromo-alpha1-(1-methylethylidene)-4-oxo-1-azetidine acetic acid Into an ice-cooled suspension of aluminum trichloride (0.400 g; 0.003 mole) in methylene chloride (15 ml) in a nitrogen current a solution of 2,3,3-tribromo-alpha-(1-methylethylidene)-4-oxo-1-azetidine acetic acid benzyl ester (0.496 g; 0.001 mole) and anisole (0.648 g, 0.65 ml, 0.006 mole) in methylene chloride (15 ml) was added drop by drop for an hour and then it was stirred at room temperature for three more hours. To the reaction mixture ethyl acetate (15 ml) and 0.1N hydrochloric acid (5 ml) were added and the layers were separated. The ethyl acetate layer was extracted with 5% sodium hydrogen carbonate solution (2×20 ml) and the layers were separated. The aqueous layer was acidified with 0.1N hydrochloric acid to pH 1, then fresh ethyl acetate (20 ml) and sodium chloride were added and the layers were again separated. The ethyl acetate layer was washed with saturated salt solution, dried and evaporated to a dry residue which crystallized upon drying at 0.1 mm Hg (0.219 g; 54.0%).

m.p. 124°–6° C. Rf=0.50 (ethyl acetate-methanol 3:1); IR (KBr): 1800(vs), 1700(s), 1630(m), 1430(m), 1370(m), 1285(m), 1245(m) cm$^{-1}$. $^1$H NMR (DMSO-d$_6$) (90 MHz) δ: 1.89 (3H, s, Me), 2.25 (3H, s, Me) and 6.73 (1H, S, C$_2$—H) ppm.

EXAMPLE 8

3,3-dibromo-2-chloro-alpha-(1-methylethylidene)-4-oxo-1-azetidine acetic acid Into an ice-cooled suspension of aluminum trichloride (1.6 g; 0.012 mole) in methylene chloride (55 ml) in a nitrogen current a solution of 3,3-dibromo-2-chloro-alpha-(1-methylethylidene)-4-oxo-1-azetidine acetic acid benzyl ester (1.5 g; 0.003 mole) and anisole (2.79 g, 2.7 ml, 0.024 mole) in methylene chloride (55 ml) was added drop by drop for an hour and then it was stirred at room temperature for three more hours. To the reaction mixture ethyl acetate (60 ml) and 0.1N hydrochloric acid (60 ml) were added and the layers were separated. The ethyl acetate layer was extracted with 5% sodium hydrogen carbonate solution (2×50 ml) and the layers were separated. The aqueous layer was acidified with 0.1N hydrochloric acid to pH 1, then fresh ethyl acetate (60 ml) and sodium chloride were added and the layers were again separated. The ethyl acetate layer was washed with brine, dried and evaporated to a dry residue, which crystallized upon drying at 0.1 mm Hg (0.931 g; 77.0%).

m.p. 106°–110° C. Rf=0.50 (ethyl acetate-methanol 3:1); IR (KBr): 1800(vs), 1700(s), 1630(m), 1430(m), 1370(m), 1285(m), 1245(m) cm$^{-1}$. $^1$H NMR (CDCl$_3$)(300 MHz) δ: 2.065 (3H, s, Me), 2.33 (3H, s, Me) and 6.27 (1H, s, C$_2$—H) and 9.57 (1H, b, COOH) ppm.

I claim:

1. Process for preparing 2-bromo- and 2-nitroxy derivatives of 3-bromo- and 3,3-dibromo-4-oxo-azetidines of the formula I

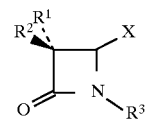

wherein

R$^1$ is hydrogen or bromine,

R$^2$ is hydrogen or bromine,

R$^3$ is

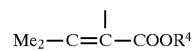

wherein R$^4$ is hydrogen, methyl, benzyl or some other carboxy-protective group, and X is bromine or nitroxy group (—ONO2), which comprises reacting penicillinic acid 1,1-dioxides of the formula II

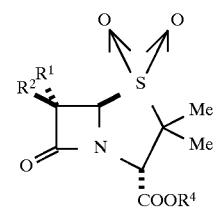

wherein

R$^1$ is hydrogen or bromine,

R$^2$ is hydrogen or bromine,

R$^4$ is methyl or benzyl or some other protective group, with DBN (1,5-diazabicyclo/3.4.0/non-5-ene) and then treating the obtained DBN salt of sulfinic acid or isolated sulfinic acid with thionyl chloride and, after eliminating thionyl chloride by evaporation passing the obtained residue through a silica gel column with a solvent as eluant or dissolving the obtained residue in a solvent and treating with tetrabutyl ammonium bromide and thereafter isolating a derivative of the formula I wherein R$^1$ is hydrogen or bromine, R$^2$ is hydrogen or bromine, $R^3$ is

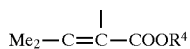

wherein $R^4$ is methyl, benzyl or some other carboxy-protective group; and

X is bromine, and optionally further reacting with silver nitrate in isopropanol and thereafter isolating derivatives of the formula I, wherein
$R^1$ is hydrogen or bromine,
$R^2$ is hydrogen or bromine,
$R^3$ is

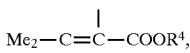

wherein $R^4$ is benzyl; and

X is nitroxy group; or alternatively
optionally reacting with anisole and $AlCl_3$ and thereafter isolating derivatives of the formula I,
wherein $R^1$ is hydrogen or bromine,
$R^2$ is hydrogen or bromine,
$R^3$ is

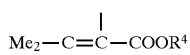

wherein $R^4$ is hydrogen and

X is bromine.

2. Process according to claim 1, characterized in that $R^1$ is hydrogen, $R^2$ is bromine, $R^3$ is

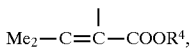

$R^4$ is meth, and X is bromine.

3. Process according to claim 1, characterized in that $R^1$ is bromine, $R^2$ is hydrogen, $R^3$ is

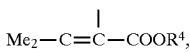

$R^4$ is methyl, and X is bromine.

4. Process according to claim 1, characterized in that $R^1$ is bromine, $R^2$ is bromine, $R^3$ is

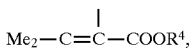

$R^4$ is methyl, and X is bromine.

5. Process according to claim 1, characterized in that $R^1$ is hydrogen, $R^2$ is bromine, $R^3$ is

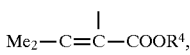

$R^4$ is benzyl, and X is bromine.

6. Process according to claim 1, characterized in that $R^1$ is bromine, $R^2$ is hydrogen, $R^3$ is

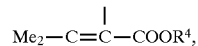

$R^4$ is benzyl, and X is bromine.

7. Process according to claim 1, characterized in that $R^1$ is bromine, $R^2$ is bromine, $R^3$ is

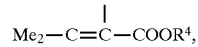

$R^4$ is benzyl, and X is bromine.

8. Process according to claim 1, characterized in that $R^1$ is hydrogen, $R^2$ is bromine, $R^3$ is

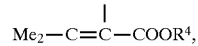

$R^4$ is hydrogen, and X is bromine.

9. Process according to claim 1, characterized in that $R^1$ is bromine, $R^2$ is hydrogen, $R^3$ is

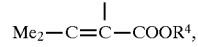

$R^4$ is hydrogen, and X is bromine.

10. Process according to claim 1, characterized in that $R^1$ is bromine, $R^2$ is bromine, $R^3$ is

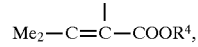

$R^4$ is hydrogen, and X is bromine.

11. Process according to claim 1, characterized in that $R^1$ is hydrogen, $R^2$ is bromine, $R^3$ is hydrogen, and X is bromine.

12. Process according to claim 1, characterized in that $R^1$ is bromine, $R^2$ is hydrogen, $R^3$ is hydrogen, and X is bromine.

13. Process according to claim 1, characterized in that $R^1$ is bromine, $R^2$ is bromine, $R^3$ is hydrogen, and X is bromine.

14. Process according to claim 1, characterized in that $R^1$ is hydrogen, $R^2$ is bromine, $R^3$ is

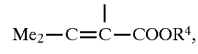

$R^4$ is methyl, and X is nitroxy.

15. Process according to claim 1, characterized in that $R^1$ is bromine, $R^2$ is hydrogen, $R^3$ is

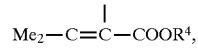

$R^4$ is methyl, and X is nitroxy.

16. Process according to claim 1, characterized in that $R^1$ is bromine, $R^2$ is bromine, $R^3$ is

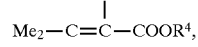

$R^4$ is methyl, and X is nitroxy.

17. Process according to claim 1, characterized in that $R^1$ is hydrogen, $R^2$ is bromine, $R^3$ is

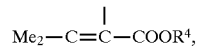
$R^4$ is benzyl, and X is nitroxy.
18. Process according to claim 1, characterized in that $R^1$ is bromine, $R^2$ is hydrogen, $R^3$ is
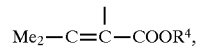
$R^4$ is benzyl, and X is nitroxy.
19. The process of claim 1 wherein said eluant is methylene chloride and said solvent for dissolving the obtained residue is tetrahydrofuran.
* * * * *

UNITED STATES PATENT AND TRADEMARK OFFICE
CERTIFICATE OF CORRECTION

PATENT NO. : 5,892,036
DATED : April 6, 1999
INVENTOR(S) : Irena Lukic

It is certified that error appears in the above-identified patent and that said Letters Patent is hereby corrected as shown below:

On the title page, item [54] and column 1, line 1, "PROCESS" should read --PROCESSES--.

Signed and Sealed this

Thirty-first Day of August, 1999

*Attest:*

Q. TODD DICKINSON

*Attesting Officer*   Acting Commissioner of Patents and Trademarks